(12) United States Patent
Bacon

(10) Patent No.: US 8,308,028 B2
(45) Date of Patent: Nov. 13, 2012

(54) DISPENSER AND RESERVOIR

(75) Inventor: Raymond John Bacon, Petersfield (GB)

(73) Assignee: Clinical Designs Limited, Hampshire (GB)

( * ) Notice: Subject to any disclaimer, the term of this patent is extended or adjusted under 35 U.S.C. 154(b) by 526 days.

(21) Appl. No.: 10/580,379

(22) PCT Filed: Nov. 19, 2004

(86) PCT No.: PCT/GB2004/004895
§ 371 (c)(1),
(2), (4) Date: Feb. 13, 2007

(87) PCT Pub. No.: WO2005/051467
PCT Pub. Date: Jun. 9, 2005

(65) Prior Publication Data
US 2007/0235469 A1    Oct. 11, 2007

(30) Foreign Application Priority Data

Nov. 21, 2003   (GB) .................................. 0327112.9

(51) Int. Cl.
*B67D 7/56*    (2010.01)
(52) U.S. Cl. ....................... 222/157; 222/158; 222/402.1
(58) Field of Classification Search .................... 222/23, 222/157, 158, 154, 156; 128/200.23; 73/323, 73/426–429; 422/501; 116/109, 227, 304
See application file for complete search history.

(56) References Cited

U.S. PATENT DOCUMENTS

| | | | |
|---|---|---|---|
| 2,002,835 A | 5/1935 | Rose | |
| 2,716,013 A | 8/1955 | Tinker | |
| 2,773,631 A | 12/1956 | Bryant | |
| 2,922,613 A | 1/1960 | Beacham et al. | |
| 2,974,835 A | 3/1961 | Herbrick | |
| 3,001,524 A * | 9/1961 | Maison et al. | 128/200.23 |
| 3,012,454 A | 12/1961 | Brodbeck | |
| 3,103,335 A | 9/1963 | Martinez | |
| 3,181,743 A | 5/1965 | Libit et al. | |
| 3,184,115 A * | 5/1965 | Meshberg | 222/156 |
| 3,187,748 A | 6/1965 | Mitchell et al. | |
| 3,190,497 A | 6/1965 | Anthon | |
| 3,294,293 A | 12/1966 | Johns | |
| 3,305,144 A | 2/1967 | Beres et al. | |

(Continued)

FOREIGN PATENT DOCUMENTS

AU    776816    7/2002

(Continued)

*Primary Examiner* — Kevin P Shaver
*Assistant Examiner* — Daniel R Shearer
(74) *Attorney, Agent, or Firm* — Ware, Fressola, Van Der Sluys & Adolphson LLP

(57) ABSTRACT

A dispenser (1) has a source (2) of medicament with a transparent reservoir (3) of glass sheathed in a transparent plastics material shrink wrapping (4), which provides an enclosure against explosion of the glass in the event of accidental breakage of the glass. The reservoir contains not only a liquid medicament (5), but also a gaseous propellant liable to cause the glass to explode if broken. A valve (6) of the source is within a body (7) of the dispenser. The valve is attached to the reservoir by a crimped on aluminum sleeve (8). With the dispenser inverted the level (14) of the medicament (5) is within the tapered tip when the medicament is close to being used up. As use of the dispenser continues, the level falls progressively faster, giving the user an indication that a fresh dispenser will soon be required.

19 Claims, 3 Drawing Sheets

U.S. PATENT DOCUMENTS

| | | | |
|---|---|---|---|
| 3,329,389 A | | 7/1967 | Clark |
| 3,395,838 A | | 8/1968 | Beres et al. |
| 3,439,846 A | | 4/1969 | Evras |
| 3,456,646 A | | 7/1969 | Phillips et al. |
| 3,506,004 A | * | 4/1970 | Mann et al. ............... 128/200.23 |
| 3,598,288 A | | 8/1971 | Posgate |
| 3,789,843 A | | 2/1974 | Armstrong et al. |
| 3,789,943 A | | 2/1974 | Kampert et al. |
| 3,913,882 A | | 10/1975 | Moulet |
| 3,926,339 A | | 12/1975 | Openchowski |
| 3,926,347 A | | 12/1975 | Low et al. |
| 4,085,616 A | * | 4/1978 | Patel et al. ..................... 600/584 |
| 4,085,886 A | | 4/1978 | Nishioka |
| 4,109,836 A | | 8/1978 | Falarde |
| 4,142,651 A | | 3/1979 | Leopoldi et al. |
| 4,354,660 A | | 10/1982 | Stupar et al. |
| 4,361,148 A | | 11/1982 | Shackleford et al. |
| 4,414,972 A | | 11/1983 | Young et al. |
| 4,457,699 A | | 7/1984 | Hattori |
| 4,570,898 A | | 2/1986 | Staeubli |
| 4,576,157 A | | 3/1986 | Raghuprasad |
| 4,620,670 A | | 11/1986 | Hughes et al. |
| 4,664,107 A | | 5/1987 | Wass |
| 4,703,761 A | | 11/1987 | Rathbone et al. |
| 4,707,038 A | | 11/1987 | Voegeli |
| 4,753,371 A | | 6/1988 | Michielin et al. |
| 4,803,978 A | | 2/1989 | Johnson, IV et al. |
| 4,817,822 A | | 4/1989 | Rand et al. |
| 4,819,834 A | | 4/1989 | Thiel |
| 4,863,379 A | | 9/1989 | Timerdahl et al. |
| 4,896,832 A | * | 1/1990 | Howlett ........................ 239/322 |
| 4,955,371 A | | 9/1990 | Zamba et al. |
| 4,972,830 A | | 11/1990 | Wong et al. |
| 5,020,527 A | | 6/1991 | Dessertine |
| 5,031,610 A | | 7/1991 | Armstrong et al. |
| 5,031,800 A | * | 7/1991 | Brunet ..................... 222/153.06 |
| 5,042,526 A | | 8/1991 | Kulakoff |
| 5,060,643 A | | 10/1991 | Rich et al. |
| 5,069,204 A | | 12/1991 | Smith et al. |
| 5,086,765 A | * | 2/1992 | Levine ..................... 128/200.21 |
| 5,098,291 A | * | 3/1992 | Curtis et al. ..................... 433/89 |
| 5,113,855 A | | 5/1992 | Newhouse |
| 5,119,806 A | | 6/1992 | Palson et al. |
| 5,152,456 A | | 10/1992 | Ross et al. |
| 5,184,761 A | | 2/1993 | Lee |
| 5,193,745 A | | 3/1993 | Holm |
| 5,217,004 A | | 6/1993 | Blasnik et al. |
| 5,224,472 A | | 7/1993 | Pesenti et al. |
| 5,239,992 A | | 8/1993 | Bougamont et al. |
| 5,273,172 A | | 12/1993 | Rossbach et al. |
| 5,295,479 A | | 3/1994 | Lankinen |
| 5,297,542 A | | 3/1994 | Bacon |
| 5,347,998 A | | 9/1994 | Hodson et al. |
| 5,370,279 A | | 12/1994 | Tardif |
| 5,388,572 A | | 2/1995 | Mulhauser et al. |
| 5,402,823 A | | 4/1995 | Cole |
| 5,408,994 A | | 4/1995 | Wass et al. |
| 5,421,482 A | | 6/1995 | Garby et al. |
| 5,447,150 A | | 9/1995 | Bacon |
| 5,469,843 A | | 11/1995 | Hodson |
| 5,487,378 A | | 1/1996 | Robertson et al. |
| 5,490,630 A | * | 2/1996 | Hecker ........................ 239/309 |
| 5,501,375 A | | 3/1996 | Nilson |
| 5,511,540 A | | 4/1996 | Bryant et al. |
| 5,546,932 A | | 8/1996 | Galli |
| 5,549,101 A | | 8/1996 | Trofast et al. |
| 5,549,226 A | | 8/1996 | Kopp |
| 5,611,444 A | | 3/1997 | Garby et al. |
| 5,623,920 A | | 4/1997 | Bryant |
| 5,645,050 A | | 7/1997 | Zierenberg et al. |
| 5,655,523 A | | 8/1997 | Hodson et al. |
| 5,667,142 A | | 9/1997 | Newman |
| 5,692,492 A | | 12/1997 | Bruna et al. |
| 5,707,038 A | | 1/1998 | Cocatre-Zilgien |
| 5,740,793 A | | 4/1998 | Hodson et al. |
| 5,772,085 A | | 6/1998 | Bryant et al. |
| 5,878,917 A | | 3/1999 | Reinhard et al. |
| 5,996,577 A | | 12/1999 | Ohki et al. |
| 6,085,742 A | | 7/2000 | Wachter et al. |
| 6,149,054 A | | 11/2000 | Cirrillo et al. |
| 6,205,999 B1 | | 3/2001 | Ivri et al. |
| 6,234,168 B1 | | 5/2001 | Bruna |
| 6,240,918 B1 | | 6/2001 | Ambrosio et al. |
| 6,253,762 B1 | | 7/2001 | Britto |
| 6,260,549 B1 | | 7/2001 | Sosiak |
| 6,283,365 B1 | | 9/2001 | Bason |
| 6,354,290 B1 | | 3/2002 | Howlett |
| 6,397,839 B1 | | 6/2002 | Stradella |
| 6,405,727 B1 | | 6/2002 | MacMichael et al. |
| 6,415,784 B1 | | 7/2002 | Christrup et al. |
| 6,422,234 B1 | | 7/2002 | Bacon |
| 6,427,683 B1 | | 8/2002 | Drachmann et al. |
| 6,431,168 B1 | | 8/2002 | Rand et al. |
| 6,439,227 B1 | | 8/2002 | Myrman et al. |
| 6,442,234 B1 | | 8/2002 | Morken et al. |
| 6,443,146 B1 | | 9/2002 | Voges |
| 6,460,537 B1 | | 10/2002 | Bryant et al. |
| 6,510,847 B1 | | 1/2003 | Helgesson et al. |
| 6,546,928 B1 | | 4/2003 | Ashurst et al. |
| 6,553,988 B1 | | 4/2003 | Holroyd |
| 6,581,590 B1 | | 6/2003 | Genova et al. |
| 6,601,582 B2 | | 8/2003 | Rand et al. |
| 6,615,827 B2 | | 9/2003 | Greenwood et al. |
| 6,637,432 B2 | | 10/2003 | Wakefield et al. |
| 6,655,379 B2 | | 12/2003 | Clark et al. |
| 6,659,307 B1 | | 12/2003 | Stradella |
| 6,755,190 B2 | | 6/2004 | Rasmussen |
| 6,866,037 B1 | | 3/2005 | Aslin et al. |
| 6,866,158 B1 | * | 3/2005 | Sommer et al. ............... 215/12.1 |
| 6,907,876 B1 | | 6/2005 | Clark et al. |
| 6,926,002 B2 | | 8/2005 | Scarrott et al. |
| 7,036,505 B2 | | 5/2006 | Bacon et al. |
| 7,093,594 B2 | | 8/2006 | Harrison et al. |
| 7,107,986 B2 | | 9/2006 | Rand et al. |
| 7,270,124 B2 | | 9/2007 | Rasmussen |
| 7,322,352 B2 | | 1/2008 | Minshull et al. |
| 7,341,057 B2 | | 3/2008 | Scarrott et al. |
| 7,387,121 B2 | | 6/2008 | Harvey |
| 7,454,267 B2 | | 11/2008 | Bonney et al. |
| 7,597,099 B2 | | 10/2009 | Jones et al. |
| 7,845,346 B2 | * | 12/2010 | Langford et al. ........ 128/200.23 |
| 2001/0013343 A1 | | 8/2001 | Andersson |
| 2002/0043262 A1 | | 4/2002 | Langford et al. |
| 2002/0056449 A1 | | 5/2002 | Wakefield et al. |
| 2003/0089368 A1 | | 5/2003 | Zhao |
| 2003/0136401 A1 | | 7/2003 | Jansen et al. |
| 2004/0025868 A1 | | 2/2004 | Bruna |
| 2004/0089299 A1 | | 5/2004 | Bonney et al. |
| 2004/0134488 A1 | | 7/2004 | Davies |
| 2004/0144798 A1 | | 7/2004 | Ouyang et al. |
| 2005/0205512 A1 | | 9/2005 | Scarrott et al. |
| 2005/0211241 A1 | * | 9/2005 | Anderson et al. ........ 128/200.22 |
| 2006/0231093 A1 | | 10/2006 | Burge et al. |
| 2006/0278225 A1 | | 12/2006 | MacMichael et al. |
| 2007/0062518 A1 | | 3/2007 | Geser et al. |
| 2007/0089735 A1 | | 4/2007 | Langfor et al. |
| 2008/0066750 A1 | | 3/2008 | Minshull et al. |

FOREIGN PATENT DOCUMENTS

| | | |
|---|---|---|
| AU | 2003234746 | 9/2003 |
| AU | 2003234748 | 9/2003 |
| DE | 629163 | 4/1936 |
| DE | 3324699 | 12/1984 |
| DE | 8715223 | 2/1988 |
| DE | 3734894 | 3/1992 |
| DE | 4111895 | 10/1992 |
| DE | 19745513 | 4/1999 |
| DE | 29818662 | 3/2000 |
| DE | 10061723 | 7/2002 |
| EP | 0312073 | 4/1989 |
| EP | 0373753 | 6/1990 |
| EP | 0414536 | 2/1991 |
| EP | 0428380 | 5/1991 |
| EP | 0501365 | 9/1992 |
| EP | 0629563 | 12/1994 |
| EP | 0764312 | 4/1998 |
| EP | 1104318 | 8/1999 |

| | | | | | | |
|---|---|---|---|---|---|---|
| EP | 1003583 | 5/2000 | | HU | 67279 | 3/1995 |
| EP | 1019125 | 7/2000 | | JP | 63251880 | 10/1988 |
| EP | 0883415 | 5/2002 | | JP | 06027550 | 4/1994 |
| EP | 1229953 | 8/2002 | | WO | WO 92/07599 | 5/1992 |
| EP | 1254678 | 11/2002 | | WO | WO 92/07600 | 5/1992 |
| EP | 1267970 | 1/2003 | | WO | WO 92/09323 | 6/1992 |
| EP | 1267975 | 1/2003 | | WO | WO 92/10229 | 6/1992 |
| EP | 1143997 | 6/2003 | | WO | WO 93/03783 | 3/1993 |
| EP | 1316365 | 6/2003 | | WO | WO 93/24167 | 12/1993 |
| EP | 1065477 | 7/2004 | | WO | WO 94/05359 | 3/1994 |
| EP | 1267974 | 6/2005 | | WO | WO 94/19042 | 9/1994 |
| EP | 1362326 | 2/2006 | | WO | WO 95/08484 | 3/1995 |
| EP | 1362325 | 8/2007 | | WO | WO 96/39337 | 12/1996 |
| FR | 2004766 | 5/1974 | | WO | WO 9711296 | 3/1997 |
| FR | 2471535 | 6/1981 | | WO | WO 98/41254 | 9/1998 |
| FR | 2483262 | 12/1981 | | WO | WO 98/52634 | 11/1998 |
| FR | 2654627 | 5/1991 | | WO | WO 99/36116 | 7/1999 |
| FR | 2660630 | 10/1991 | | WO | WO 00/01436 | 1/2000 |
| FR | 2701653 | 8/1994 | | WO | WO 01/32247 | 5/2001 |
| GB | 161969 | 7/1922 | | WO | WO 02/38207 | 5/2002 |
| GB | 727195 | 3/1955 | | WO | WO 02/43794 | 6/2002 |
| GB | 939324 | 10/1963 | | WO | WO 02/053295 | 7/2002 |
| GB | 997617 | 7/1965 | | WO | WO 02/058771 | 8/2002 |
| GB | 1012565 | 12/1965 | | WO | WO 02/058772 | 8/2002 |
| GB | 1269811 | 4/1972 | | WO | WO 02/078595 | 10/2002 |
| GB | 1403826 | 8/1975 | | WO | WO 03/010154 | 2/2003 |
| GB | 2079183 | 1/1982 | | WO | WO 03/012565 | 2/2003 |
| GB | 2191032 | 12/1987 | | WO | WO 03/080161 | 10/2003 |
| GB | 2233236 | 1/1991 | | WO | WO 03/086518 | 10/2003 |
| GB | 2262452 | 6/1993 | | WO | WO 2004/022142 | 3/2004 |
| GB | 2263873 | 8/1993 | | WO | WO 2004/022143 | 3/2004 |
| GB | 2264238 | 8/1993 | | WO | WO 2004/022242 | 3/2004 |
| GB | 2266466 | 11/1993 | | WO | WO 2004/078236 | 9/2004 |
| GB | 2279571 | 1/1995 | | WO | WO 2005/002654 | 1/2005 |
| GB | 2279879 | 1/1995 | | WO | WO 2005/041850 | 5/2005 |
| GB | 2292891 | 3/1996 | | | | |
| GB | 2366519 | 3/2002 | | | | |

\* cited by examiner

US 8,308,028 B2

DISPENSER AND RESERVOIR

CROSS REFERENCE TO RELATED APPLICATIONS

This application is for entry into the U.S. national phase under §371 for International Application No. PCT/GB04/004895 having an international filing date of Nov. 19, 2004, and from which priority is claimed under all applicable sections of Title 35 of the United States Code including, but not limited to, Sections 120, 363 and 365(c), and which in turn claims priority under 35 USC §119 to U.K. Patent Application No. 0327112.9 filed on Nov. 21, 2003.

TECHNICAL FIELD

The present invention relates to a dispenser, particularly though not exclusively for dispensing aerosol or powder borne medicaments, and to a source reservoir for such a dispenser.

BACKGROUND OF THE INVENTION

I have applied for a number of patents on dispensers for a gaseous, gas borne or droplet substance. In particular, in my prior International Patent Application, PCT/GB98/00770, at least as amended on entry in the European Regional Phase, there is described and claimed:

A dispenser for a gaseous, gas borne or droplet substance, the dispenser including:
  a body having a mouthpiece with an inhalation/insufflation orifice at its end;
  a junction in the body for a source of gas or evaporable liquid comprising or containing the said substance (the source being carried by the body); and
  a breath actuatable valve, for controlling the release of said gas or liquid, comprising:
  a valve inlet connected to the junction;
  a valve outlet;
  a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
  a movable member, for moving the movable portion of the tube to control its kinking, and being movably mounted in the body for movement by the act of inhalation from a rest position towards the orifice—or at least in the direction of air flow through the dispenser;
  the tube being kinked to an obturating extent when the movable member is in a rest position and un-kinked when the movable member is moved on inhalation for release of the gas or liquid.

Such a dispenser can loosely be classed as a breath actuated, kink valve dispenser and is referred to herein as "My Earlier Breath Actuated, Kink Valve Dispenser".

With such a dispenser, in common with others of my design and other designs, there is advantage to the user in knowing how many doses are left in the reservoir of the substance source, the reservoir typically being an aerosol valve can, the can being an aluminium pressing.

Two approaches to dose measurement are known.

Firstly, dispensers actuated by depression of the end of the can towards the body of the dispenser body can be provided with electronic or mechanical counters which sense the number of depressions and count down to indicate exhaustion of the dispenser. This approach is costly.

A second approach is to provide the source with a transparent reservoir, typically of glass. Existing glass reservoirs have replicated the shape of the prior pressed aluminium can. Their shape renders difficult estimation of the number of doses remaining.

SUMMARY OF THE INVENTION

The object of the present invention is to provide dispenser having a reservoir whose content can be readily estimate, particularly as it approaches exhaustion.

According to one aspect of the invention there is provided a dispenser for a gaseous, gas borne or droplet substance having a source of the substance, the source having a reservoir with:
  a major portion having a comparatively large cross-section of its substance space and
  a minor portion having a comparatively small cross-section of its substance space,
the reservoir being translucent, and preferably transparent, at the minor portion at least, whereby a user can note a comparatively rapid depletion with use of the quantity of substance remaining when the source approaches exhaustion of the substance.

According to a second aspect of the invention there is provided a source for a dispenser of a gaseous, gas borne or droplet substance from the source, the source having a reservoir with:
  a major portion having a comparatively large cross-section of its substance space and
  a minor portion having a comparatively small cross-section of its substance space,
the reservoir being translucent, and preferably transparent, at the minor portion at least, whereby a user can note a comparatively rapid depletion with use of the quantity of substance remaining when the source approaches exhaustion of the substance.

According to a third aspect of the invention there is provided a reservoir for a source of a gaseous, gas borne or droplet substance to be used in a dispenser, the reservoir having:
  a major portion having a comparatively large cross-section of its substance space and
  a minor portion having a comparatively small cross-section of its substance space,
the reservoir being translucent, and preferably transparent, at the minor portion at least, whereby a user can note a comparatively rapid depletion with use of the quantity of substance remaining when the source approaches exhaustion of the substance.

The minor portion can have a constant cross-section or a progressively diminishing cross-section, whereby the rate of fall of the level of the substance increases as it is further depleted.

Normally the minor portion will be at the opposite end of the source from its release valve, with the user holding the dispenser valve-up to observe the level of the substance in the minor portion. However, the minor portion could be provided at the valve end of the reservoir as a diminishing cross-section neck.

The reservoir can be of glass or transparent/translucent plastics material. Where it is of glass, this can be enclosed in a plastics material sheath, typically a shrink wrapping or an insert moulding, i.e. a moulding of the plastics material sheath onto the glass reservoir within a mould tool. Where the minor portion is to have a cross-section so small as to be impractical to form in glass, in production with sufficient precision, it is envisaged that the reservoir as such can be provided as a plastics material moulding, possibly enclosed by a robust, impermeable outer enclosure, such as a glass casing, itself enclosed in a shrink wrapping or an insert moulding for instance.

Alternatively, the reservoir can be provided with an insert, which substantially reduces the cross-section thereof, typically at its end distal from the valve. Again, the insert can be at the valve end. In either case the insert can be formed as part of a component of the valve in the source for metering a dose from its reservoir. The insert can be parallel or tapered, the latter shape providing an increasing rate of fall with depletion.

BRIEF DESCRIPTION OF THE DRAWINGS

To help understanding of the invention, various specific embodiments thereof will now be described by way of example and with reference to the accompanying drawings, in which.

DETAILED DESCRIPTION

Figure 1:
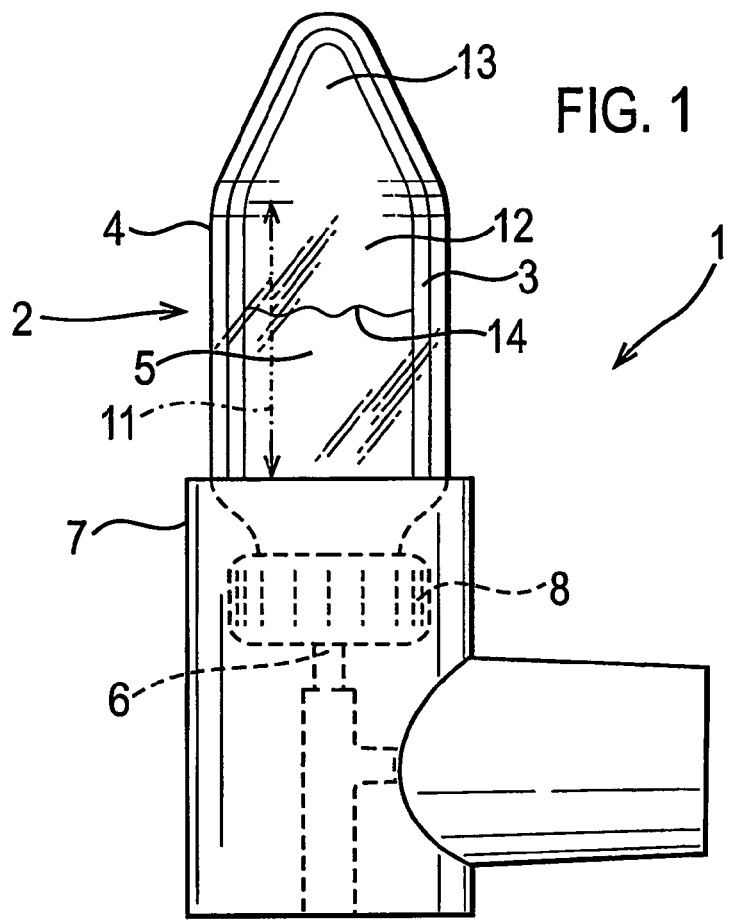
FIG. 1 is a side view of a dispenser according to the invention.

Referring to FIG. 1, the dispenser 1 has a source 2 of medicament with a transparent reservoir 3 of glass sheathed in a transparent plastics material shrink wrapping 4, which provides an enclosure against explosion of the glass in the event of accidental breakage of the glass. The reservoir contains not only a liquid medicament 5, but also a gaseous propellant liable to cause the glass to explode if broken.

A valve 6 of the source, shown only in outline in FIG. 1, is within a body 7 of the dispenser. The valve is attached to the reservoir by a crimped-on aluminium sleeve 8.

The reservoir is parallel 11 through much of its length, where it has a comparatively large cross-section of its substance space 12, but has a tapered tip 13 remote from the valve 6, where it has a comparatively smaller and decreasing cross-section.

Figure 2:
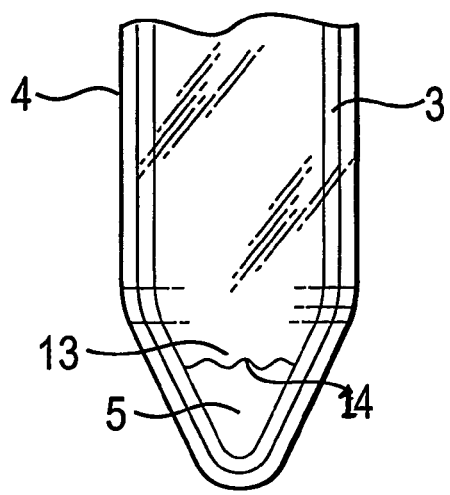
FIG. 2 is a scrap view of the reservoir of the dispenser of FIG. 1, inverted and approaching depletion.

With the dispenser inverted, FIG. 2, the level 14 of the medicament 5 is within the tapered tip when the medicament is close to being used up. As use of the dispenser continues, the level falls progressively faster, giving the user an indication that a fresh dispenser will soon be required. Typically the user will take a fresh dispenser with him when the level is such as to indicate that the daily number of doses will exhaust the reservoir.

Figure 3:
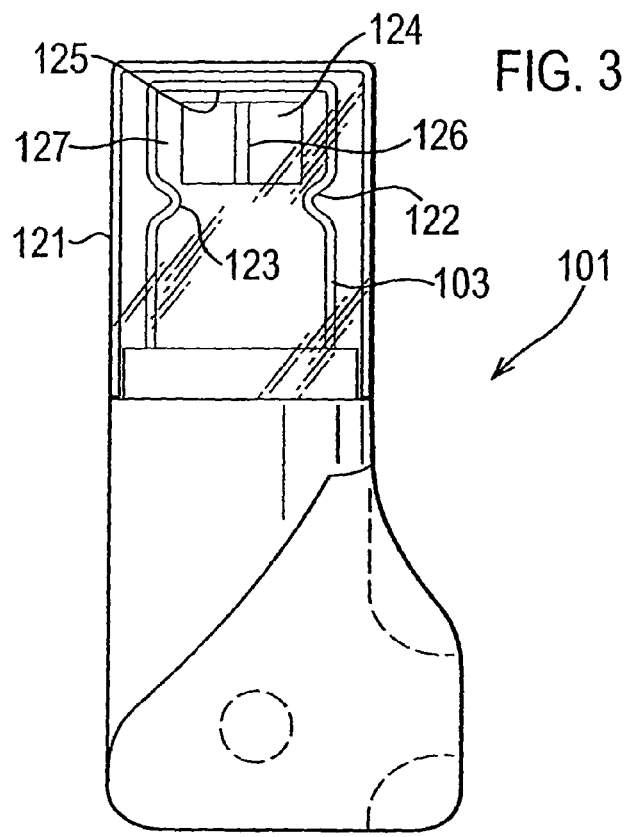
FIG. 3 is a view similar to FIG. 1 of another dispenser of the invention.

Turning to FIG. 3, the dispenser 101 there shown has a glass reservoir 103 within a welded-on transparent cover 121, welded at a position appropriate for its breath actuated, kink valve mechanism, such as disclosed in my patent application No. PCT/GB03/001102. The reservoir has indents 122 in the glass which provides dimples 123 on the inside surface of the reservoir. An opaque plastics material slug 124 is pushed past the dimples, to be held by the dimple against an end 125 of the reservoir. The slug has a ribs 126 keeping it centred in the reservoir and a diameter such that the peripheral space between the slug and the inner wall of the reservoir has a considerably reduced cross-section in comparison with that of the reservoir where the slug is not present.

Figure 5:
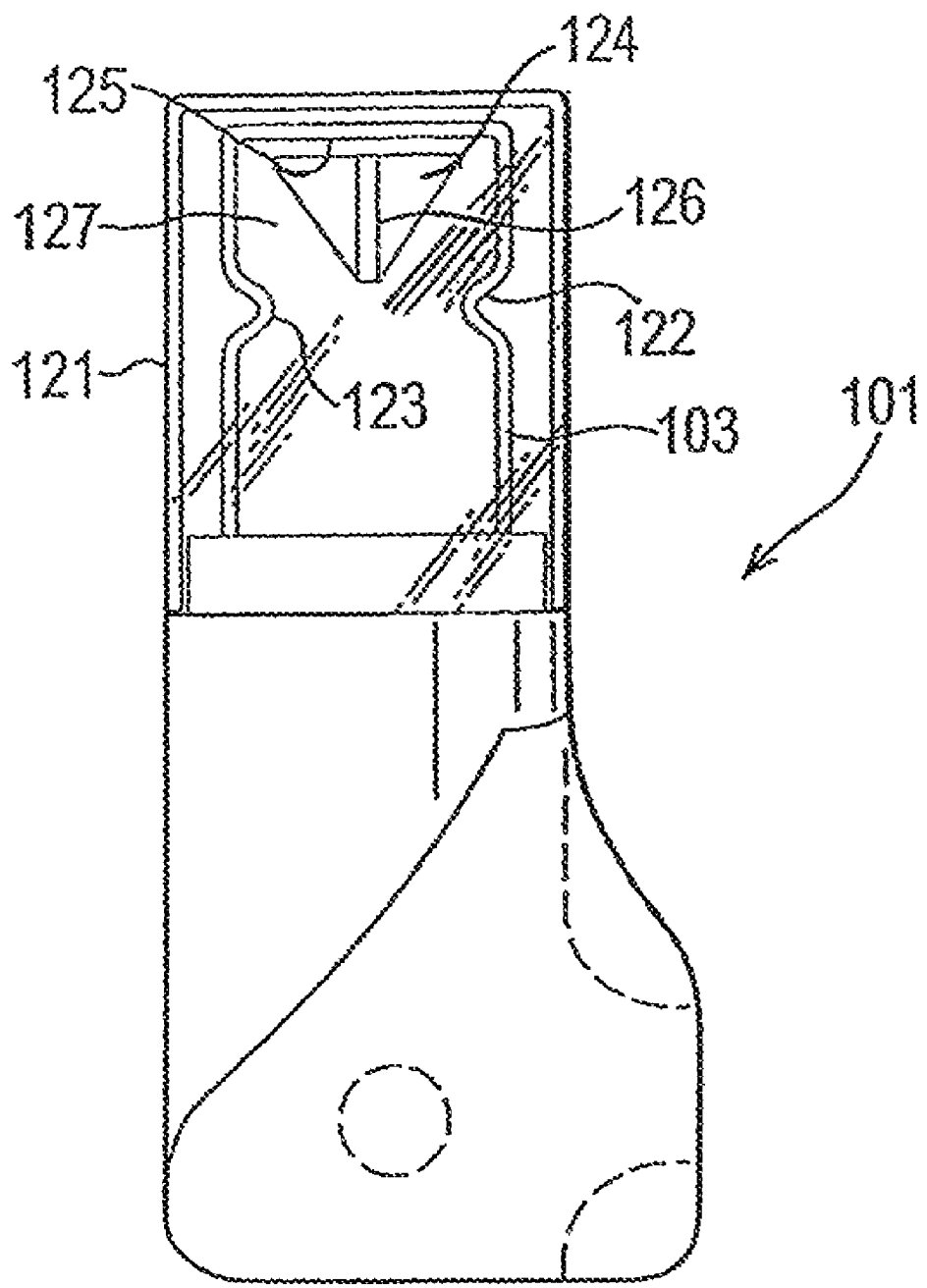
FIG. 5 is a view similar to FIG. 3 showing an insert/slug that is tapered.

As the source approaches exhaustion, the level observed in the reservoir when inverted drops to be in slug/glass annulus 127. As in the FIG. 1 embodiment, this gives a good indication of impending exhaustion. FIG. 5 shows an embodiment of the dispenser where the slug 124 is tapered.

Figure 4:
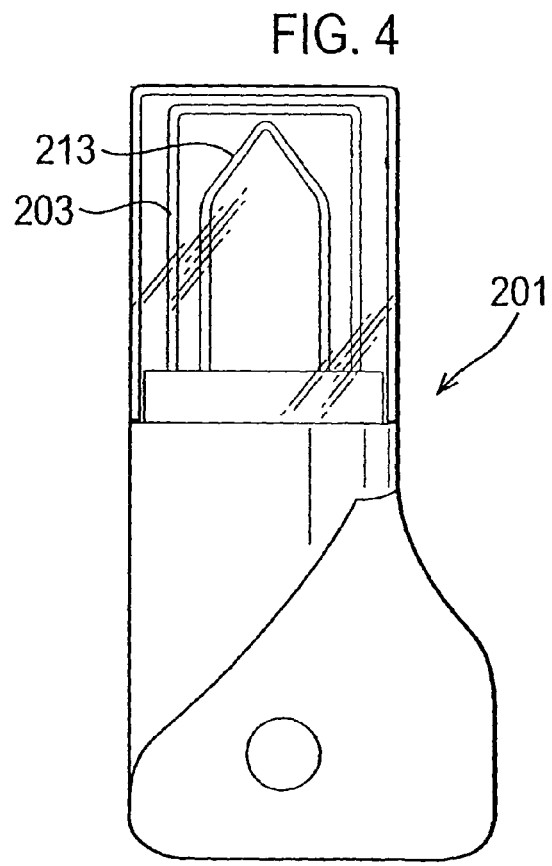
FIG. 4 is a similar view of a third dispenser of the invention.

Turning now to FIG. 4, the dispenser 201 there shown again has a parallel glass reservoir 203. Within it is a translucent plastics material lining of a shape essentially similar to that of the reservoir 3, i.e. with a tip 213 of lesser cross-section. The exhaustion level can be observed in this also.

The invention claimed is:

1. A dispenser for a gaseous, gas borne or droplet substance comprising a source of the substance, wherein said substance comprises medicament and propellant and said source comprises a reservoir and a release valve, wherein said reservoir comprises:
   a major portion having a comparatively large cross-section of its substance space and
   a minor portion provided with an insert which substantially reduces the cross-section thereof so that said minor portion has a comparatively small cross-section of its substance space,
the reservoir being translucent or transparent, at the minor portion at least, and the minor portion is at an opposite end of the source from the release valve, so that during use in the valve-down position the medicament flows away from the minor portion and a user inverting the dispenser so it is valve up can observe the level of the substance in the minor portion and can note a comparatively rapid depletion with use of the quantity of substance remaining when the source approaches exhaustion of the substance.

2. The dispenser as claimed in claim 1, wherein the minor portion of the reservoir has a progressively diminishing cross-section, whereby the rate of fall of the level of the substance increases as it is further depleted.

3. The dispenser as claimed in claim 1, wherein the reservoir is of glass.

4. The dispenser as claimed in claim 3, wherein the glass reservoir is enclosed in a plastics material sheath.

5. The dispenser as claimed in claim 4, wherein the plastics material sheath is a shrink wrapping or an insert moulding.

6. The dispenser as claimed in claim 1, wherein the reservoir is of transparent/translucent plastics material.

7. The dispenser as claimed in claim 6, wherein the reservoir is enclosed by a robust, impermeable outer enclosure.

8. The dispenser as claimed in claim 1, wherein the reservoir is transparent at the minor portion at least.

9. The dispenser as claimed in claim 1, wherein the minor portion of the reservoir has a constant cross-section.

10. The dispenser as claimed in claim 1, wherein the insert includes a uniform cross-section.

11. The dispenser as claimed in claim 1, wherein the insert is tapered.

12. A dispenser for a gaseous, gas borne or droplet substance comprising a source of the substance, wherein said substance comprises medicament and propellant and said source comprises a reservoir and a release valve, wherein said reservoir comprises:
   indents providing dimples on the inside surface of said reservoir thereby forming a glass annulus at the end of said reservoir; and,
   a slug to be held by said dimples against said glass annulus;
the reservoir being translucent or transparent, at least at said glass annulus, and said end of the reservoir is at an opposite end of the source from the release valve, so that during use in the valve-down position the medicament flows away from said end of the reservoir and a user inverting the dispenser so it is valve up can observe the level of the substance in said glass annulus and can note a comparatively rapid depletion with use of the quantity of substance remaining when the source approaches exhaustion of the substance.

13. The dispenser as claimed in claim 12, wherein said slug substantially reduces the cross-section of said resevoir.

14. The dispenser as claimed in claim 13, wherein the slug includes a uniform cross-section.

15. The dispenser as claimed in claim 13, wherein the slug is tapered.

16. The dispenser as claimed in claim 12, wherein the reservoir is of glass.

17. The dispenser as claimed in claim 16, wherein the glass reservoir is enclosed in a plastic material sheath.

18. The dispenser as claimed in claim 17, wherein the plastics material sheath is a shrink wrapping or an insert moulding.

19. The dispenser as claimed in claim 12, wherein the reservoir is transparent at least at said glass annulus.

* * * * *